(12) United States Patent  (10) Patent No.: US 7,590,216 B2
Katsevich  (45) Date of Patent: Sep. 15, 2009

(54) CONE BEAM LOCAL TOMOGRAPHY

(75) Inventor: Alexander Katsevich, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 332 days.

(21) Appl. No.: 11/581,160

(22) Filed: Oct. 13, 2006

(65) Prior Publication Data

US 2007/0147575 A1  Jun. 28, 2007

Related U.S. Application Data

(60) Provisional application No. 60/754,236, filed on Dec. 28, 2005.

(51) Int. Cl.
*A61B 6/03* (2006.01)
(52) U.S. Cl. .......................... 378/4; 378/901
(58) Field of Classification Search ............... 378/4, 378/15, 901; 382/128–131
See application file for complete search history.

(56) References Cited

U.S. PATENT DOCUMENTS

| | | | |
|---|---|---|---|
| 5,539,800 A | 7/1996 | Katsevich et al. | 378/210 |
| 5,550,892 A | 8/1996 | Katsevich et al. | 378/210 |
| 5,717,211 A | 2/1998 | Katsevich | 250/363.04 |
| 6,526,117 B1 * | 2/2003 | Okerlund et al. | 378/8 |
| 6,574,299 B1 | 6/2003 | Katsevich | 378/15 |
| 6,771,733 B2 | 8/2004 | Katsevich | 378/4 |
| 6,804,321 B2 | 10/2004 | Katsevich | 378/4 |
| 6,898,264 B2 | 5/2005 | Katsevich | 378/4 |
| 7,010,079 B2 | 3/2006 | Katsevich | 378/4 |
| 2006/0140335 A1 * | 6/2006 | Heuscher et al. | 378/4 |

OTHER PUBLICATIONS

Kudo et al., Exact and Approximate algorithms for helical cone-beam CT, Jun. 17, 2004, Physics in Medicine and Biology, vol. 49, pp. 2913-2931.*

A. Katsevich, S. Basu, Jiang Hsieh, "Exact filtered backprojection reconstruction for dynamic pitch helical cone beam computed tomography," Phys. Med. Biol., vol. 49, (2004) pp. 3089-3103.

(Continued)

*Primary Examiner*—Edward J Glick
*Assistant Examiner*—John M Corbett
(74) *Attorney, Agent, or Firm*—Brian S. Steinberger; Phyllis K. Wood; Law Offices of Brian S. Steinberger, P.A.

(57) ABSTRACT

Methods, systems and processes for providing efficient image reconstruction using local cone beam tomography which provide a reduced level of artifacts without suppressing the strength of the useful features; and in a dynamic case provide reconstruction of objects that are undergoing a change during the scan. An embodiment provides a method of reconstructing an image from cone beam data provided by at least one detector. The method includes collecting CB projection data of an object, storing the CB projection data in a memory; and reconstructing the image from the local CB projection data. In the reconstructing step, a combination of derivatives of the CB projection data that will result in suppressing the artifacts are found. The combination of derivatives includes collecting cone beam data that represents a collection of integrals that represent the object.

15 Claims, 7 Drawing Sheets

OTHER PUBLICATIONS

F. Noo, Jed Pack, D. Heuscher, "Exact helical reconstruction using native cone-beam geometries," Phys. Med. Biol. vol. 48, (2003), pp. 3787-3818.

Alexander Katsevich, "Improved cone beam local tomography," Inverse Problems, vol. 22, (2006), pp. 627-643.

Alexander Katsevich, "Cone Beam Local Tomography," SIAM J. Appl. Math, vol. 59, No. 6, pp. 2224-2246.

Y. Bresler, J. Broksih, "A hierarchical algorithm for fast backprojection in helical cone-beam tomography," IEEE, (2004), pp. 1420-1423.

D. L. Marks, R. Stack, A. J. Johnson, D. J. Brady, D. C. Munson, Jr., "Cone-beam tomography with a digital camera," Applied Optics, vol. 40, No. 11, Apr. 10, 2001, pp. 1795-1804.

G. L. Zeng, Yi Weng, G. T. Gulberg, "Iterative Reconstruction with Attenuatio Compensation from Cone-Beam Projections Acquired via Nonplanar Orbits," IEEE, vol. 44, No. 1, Feb. 1997, 9 pages.

G. L. Zeng, R. Clack, G. T. Gullberg, "Implementation of Tuy's cone-beam inversion formula," Phys. Med. Biol. vol. 39 (1994), pp. 493-507.

* cited by examiner

CONE BEAM LOCAL TOMOGRAPHY

This Patent Application claims the benefit of priority to U.S. Provisional Patent Application No. 60/754,236 filed on Dec. 28, 2005 and was funded in part by NSF grant DMS-0104033 and the Alexander von Humboldt Foundation.

FIELD OF THE INVENTION

This invention relates to local tomography and, in particular, to methods, systems, apparatus and devices for cone beam local tomography.

BACKGROUND AND PRIOR ART

In computed tomography (CT) the goal is to reconstruct the distribution of the x-ray attenuation coefficient $f$ inside the object being scanned. Local tomography (LT) computes not $f$, but $Bf$, where B is some operator that enhances singularities of $f$. In two dimensions (2D), B is an elliptic pseudo-differential operator (PDO) of order one as described by A. Katsevich, "Local Tomography for the Generalized Random Transform", SIAM Journal on Applied Mathematics, Vol. 57, no. 4 (1997) pp. 1128-1162, Kuchment et al., "On local Tomography", Inverse Problem 11 (1995), pp. 571-589, A. Ramm and A. Katsevich, "The Random Transform and Local Tomography", CRC Press, Boca Raton, Fla., 1996 and A. G. Ramm, "Necessary and Sufficient Conditions for a PDO to be a local tomography operator", Comptes Rend Acad. Sci., Paris 332 (1996) pp. 613-618. In the cone beam setting (three dimensions) a LT function is denoted by $g_A$. The corresponding operator B: $f \rightarrow g_A$ is much more complicated than in 2D. It preserves the so-called visible (or, useful) singularities and creates non-local artifacts. Unfortunately, the strength of these artifacts is the same as that of the useful singularities of $g_A$ as described in A. Katsevich "Cone Beam Local Tomography", SIAM Journal on Applied Mathematics (1999), pp. 2224-2246 and D. Finch et al, "Microlocal analysis of the X-ray transform with sources on a curve", Inside out: Inverse Problems and Applications, Cambridge Univ. Press, (2003) pp. 193-218.

SUMMARY OF THE INVENTION

A primary objective of the invention is to provide a new method, system, apparatus and device for improved cone beam local tomography.

A secondary objective of the invention is to provide new methods, systems, apparatus and devices for cone beam local tomography that produces artifacts that are one order smoother in the scale of Sobolev spaces.

A third objective of the invention is to provide new methods, systems, apparatus and devices for cone beam local tomography using the flexibility of LT, its relative stability with respect to inconsistencies in the data and the ability to accurately reconstruct edges inside objects, which provides important information complementing well-established inversion techniques.

A fourth objective of the invention is to provide methods, systems, apparatus, and devices for reconstructing an image from local cone beam projection data with suppressed artifacts.

A fifth objective of the invention is to provide methods, systems, apparatus, and devices for reconstructing an image from local cone beam projection data with suppressed artifacts without suppressing the useful features of the image.

A sixth objective of the invention is to provide methods, systems, apparatus, and devices for determining a shift between a location of the reconstruction point shown on the reconstructed image and an actual location of the point to determine a location error of the moving object to correct the location of the useful features of the actual image.

A first embodiment provides a method of reconstructing an image from cone beam data provided by at least one detector. First, cone beam projection data of an object is collected and stored in memory. The image is reconstructed from the local cone beam projection data, wherein artifacts of the image are suppressed without suppressing the strength of the useful features. During the reconstructing step, a direction of a derivative of the cone beam projection data that will result in suppressing the artifacts is found, the direction being a tangent to the curve, which represents the scan trajectory. Based on the direction, the cone beam projection data is differentiated along the direction of the tangent of the curve. The derivative results are processed, then back projection is applied to the processed data to extract the useful features of the image with suppressed artifacts.

In an embodiment, a shift between a location of the reconstruction point shown on the reconstructed image and an actual location of the point in the object is determined to correct for the location of the useful features of the actual image.

Further objects and advantages of this invention will be apparent from the following detailed description of preferred embodiments which are illustrated schematically in the accompanying drawings.

DESCRIPTION OF THE PREFERRED EMBODIMENTS

Figure 1:
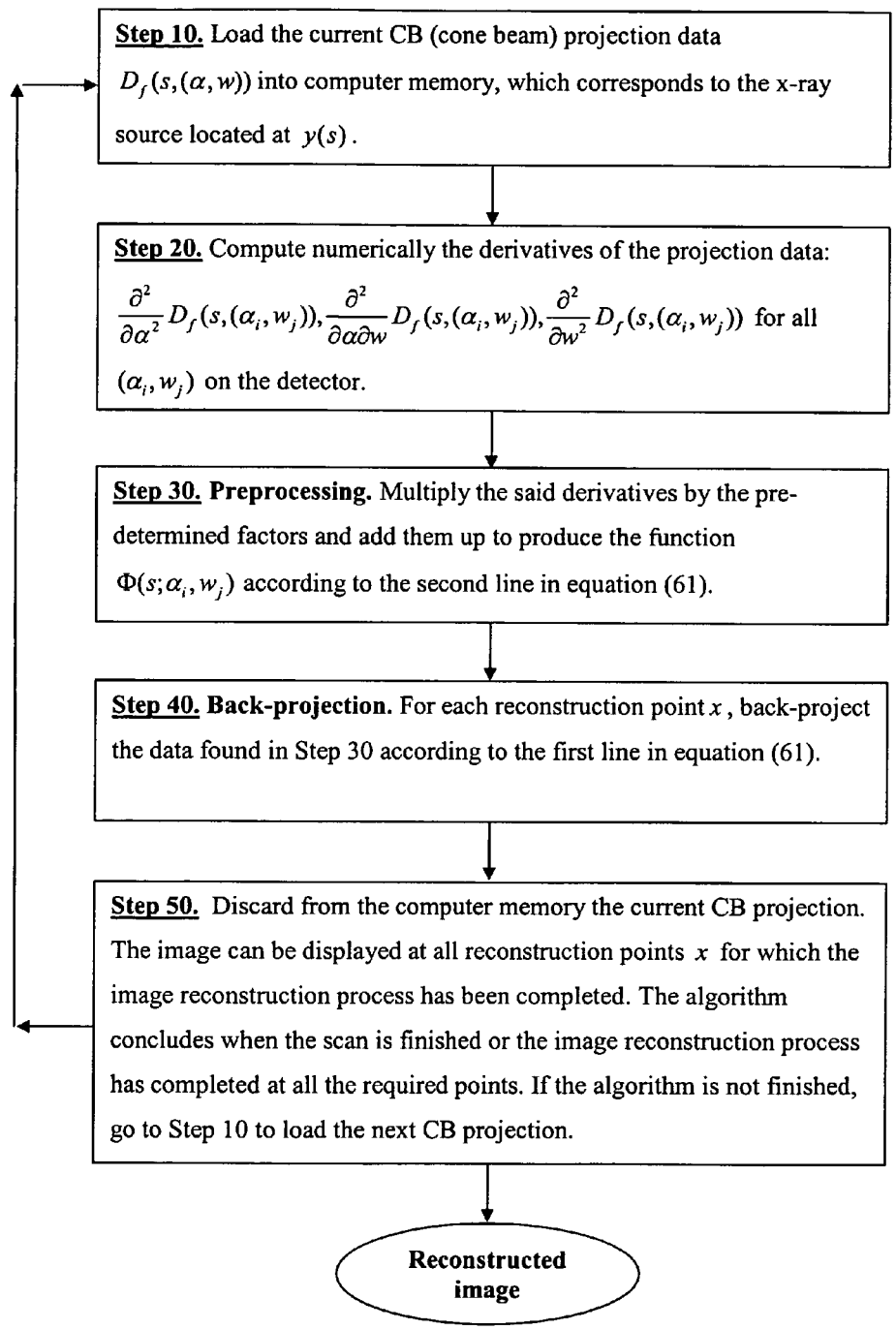
FIG. 1 shows an overview of the basic process steps according to the invention.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Local Tomography Function of the Present Invention:
  C is a smooth curve defined by $I \ni s \to y(s) \subset R^3$. Here
  s is a real parameter;
  I is a compact interval;
  y(s) denote the parametric equations of the curve; and
  $R^3$ is the three-dimensional Euclidean space.

Fix an open set V, whose closure $\overline{V} \subset R^3 \setminus C$. Let $D_f(s,\alpha)$ denote the cone beam transform of $f$:

$$D_f(s, \alpha) = \int_0^\infty f(y(s) + \alpha t) dt, \; s \in I, \; \alpha \in S^2, \quad (1)$$

where $f \in C_0^\infty(V)$. Here
  $\alpha$ is a unit vector;
  $S^2$ is the unit sphere in $R^3$; and
  $f$ is the function representing the distribution of the x-ray attenuation coefficient inside the object being scanned Fix $\phi \in C_0^\infty(I \times V)$ and define:

$$g(x) := Bf(x) := \int_I \varphi(s, x) \frac{\partial^2}{\partial q^2} D_f(s, \beta(q, x)) \Big|_{q=s} ds, \quad (2)$$

where q is real parameter and $$\beta(q, x) := \frac{x - y(q)}{|x - y(q)|}. \quad (3)$$

g(x) defined by equation (2) above is one example of a new local tomography function of the present invention. Introduce the following notation $\Pi(x,\xi) := \{y \in R^3 : \xi \cdot (y-x) = 0\}$, $WF_v(f) := \{(x,\xi) \in WF(f) : \Pi(x,\xi) \text{ intersects } C \text{ transversely}\}$, $L_+(s,z) := \{x \in R^3 : x = y(s) + t(z - y(s)), t > 0\}. \quad (4)$ Here
  $\xi$ is a non-zero vector in $R^3$;
  z is a point in $R^3$;
  WF(f) is the wave-front of $f$; and
  $WF_v(f)$ denotes the visible singularities of $f$. The set $WF_v(f)$ and the term 'visible singularity' were introduced in E. T. Quinto, "Singularies of the X-ray transform and limited data tomography in $R^2$ and $R^3$", SIAM Journal of Mathematical Analysis, vol. 24 (1993), pp. 1215-1225.

Analogously to A. Katsevich, "Cone beam local tomography", SIAM Journal on Applied Mathematics, vol. 59 (1999), pp. 2224-2246, the following results can be established: the operator B defined by equation (2) extends to a map $E'(V) \to E'(V)$, and $WF(g) \subset WF_v(f) \cup E(f,C)$, $E(f,C) := \{(x,\xi) \in T^*V \setminus 0 : \xi \perp \dot{y}(s), \xi \perp (x - y(s)), x \in L_+(s,z), (z,\xi) \in WF(f), (s,x) \in \text{supp}\phi\}. \quad (5)$ Here E'(V) is the space of distributions with compact support inside V, and V is an open set not intersecting C.

An equivalent definition of the set E(f,C) is as follows. If $(z,\xi) \in WF(f)$ and the plane $\Pi(z,\xi)$ is tangent to C at some point y(s), then $(x,\xi) \in E(f,C)$ for all $x \in L_+(s,z)$, $(s,x) \in \text{supp}\phi$.

$\xi^{(0)} \neq 0$ and $x^{(0)} \in R^3 \setminus C$ are selected such that the plane $\Pi(x^{(0)},\xi^{(0)})$ intersects C transversely. Then there exists a sufficiently small conic neighborhood $U \times \Omega \subset T^*V \setminus 0$ of $(x^{(0)},\xi^{(0)})$ such that $B(x,\xi)$ is a classical amplitude from the class $S^1(U \times \Omega)$. Moreover, if $\Pi(x^{(0)},\xi^{(0)})$ does not intersect C, then $B(x,\xi)$ is from the class $S^{-\infty}(U \times \Omega)$ for some neighborhood $U \times \Omega \ni (x^{(0)},\xi^{(0)})$.

The principal symbol of B is computed as follows. Denote $$m := \inf_{(s,x) \in \text{supp}\varphi} |x - y(s)|, \; M := \sup_{(s,x) \in \text{supp}\varphi} |x - y(s)|, \quad (6)$$

and pick $\delta$, $0 < \delta < m$. Let w(t) be a function with the properties $w(t) \in C_0^\infty([m-\delta, M+\delta]), w(t) = 1, t \in [m,M]. \quad (7)$ Representing $f$ in terms of its Fourier transform and using equation (7) we get from equations (1) and (2)

$$g(x) = \frac{1}{(2\pi)^3} \int_{R^3} \tilde{f}(\xi) \quad (8)$$

$$\int_{R^2} \varphi(s, x) \times \frac{\partial^2}{\partial q^2} w(t|x - y(q)|) |x - y(q)| e^{-i\xi \cdot (y(s) + t(x - y(q)))} \Big|_{q=s}$$

$$dt ds d\xi = \frac{1}{(2\pi)^3} \int_{R^3} \tilde{f}(\xi) B(x, \xi) e^{-i\xi \cdot x} d\xi,$$

where $$B(x, \xi) = -\int_{R^2} \varphi(s, x) [w(t|x - y(s)|) |x - y(s)| (t\xi \cdot \dot{y}(s))^2 + O(\xi)] \times \quad (9)$$

$$e^{-i\xi \cdot (x - y(s))(t-1)} dt ds.$$

Pick $(x,\xi) \in T^*V \setminus 0$ such that $\Pi(x,\xi)$ intersects C, and the intersections are transversal. Asymptotics of $B(x,\sigma\xi)$ as $\sigma \to \infty$ are found. Here $\sigma$ is a real parameter. The stationary points of the phase in equation (9) are determined by solving $(\xi \cdot \dot{y}(s))(t-1) = 0, \; \xi \cdot (x - y(s)) = 0 \quad (10)$ for s and t. Let $s_j = s_j(x,\xi)$ be the points of intersections of the plane $\Pi(x,\xi)$ and curve C. As is easily seen, the critical points are $(s=s_j, t=1)$. They are non-degenerate, because by assumption $\xi \cdot \dot{y}(s_j) \neq 0$. Now the stationary phase method immediately yields $$B(x, \sigma\xi) = -2\pi\sigma \sum_j \varphi(s_j, x) |x - y(s_j)| |\xi \cdot \dot{y}(s_j)| + O(1), \; \sigma \to \infty. \quad (11)$$

Analysis of Artifacts:

Pick any $(z^{(0)}, \xi^{(0)}) \in WF(f)$ such that the plane $\Pi(z^{(0)}, \xi^{(0)})$ is tangent to C at some $y(s_0)$. Fix $x^{(0)} \in L_+(s_0, z^{(0)})$, $x^{(0)} \notin \{z^{(0)}, y(s_0)\}$ and $(s_0, x^{(0)}) \in \text{supp}\phi$. The problem is to find the behavior of g, defined by equation (2), in a neighborhood of $x^{(0)}$. This behavior, of course, depends on the nature of the singularity of $f$ at $z^{(0)}$. Assuming that $f$ is a conormal distribution associated to a smooth hypersurface S, which has nonzero Gaussian curvature at $z^{(0)}$: $f \in I_{comp}^m(V, N^*S)$ for some m. Here $N^*S$ is the conormal bundle of S. Let $U \times \Omega$ be a sufficiently small conic neighborhood of $(z^{(0)}, \xi^{(0)})$. In view of the above examples, it is assumed without loss of generality that $\hat{f}(\xi) = A(\xi)e^{iH(\xi)} + A_1(\xi)$ (cf. L. Hormander, The Analysis of Linear Partial Differential Operators, Volume IV, Springer Verlag, New York, 1985, Proposition 25.1.3). Here $A \in S^{m-3/4}(R^3)$ and $A(\xi) \equiv 0$ on $R^3 \setminus \Omega$, $A_1 \in S^{-\infty}(R^3)$, $H(\xi) \in C_0^\infty(R^3 \setminus 0)$ is real-valued and homogeneous of degree one, and $N^*S = (H'(\xi), \xi)$ on $U \times \Omega$.

The coordinate system is introduced with the origin at $z^{(0)}$, such that $\xi^{(0)}$ is along the $x_3$-axis, and $y(s_0) = (c, 0, 0)$, where $c = |y(s_0) - z^{(0)}|$. Then $$x^{(0)} = (b, 0, 0), \dot{y}_3(s_0) = 0, \dot{y}_2(s_0) \neq 0;$$
$$H_3(\xi^{(0)}) = H_{j3}(\xi^{(0)}) = 0, j = 1, 2, 3;$$
$$\begin{vmatrix} H_{11}(\xi^{(0)}) & H_{12}(\xi^{(0)}) \\ H_{21}(\xi^{(0)}) & H_{22}(\xi^{(0)}) \end{vmatrix} \neq 0.$$
(12)

The inequality $\dot{y}_2(s_0) \neq 0$ is equivalent to the assumption that the line tangent to C at $y(s_0)$ does not contain $z^{(0)}$. This assumption is not very restrictive, because almost all scanning protocols satisfy it. By assumption, $x^{(0)} \notin \{z^{(0)}, y(s_0)\}$, so $b \notin \{0, c\}$. Denote $\phi_1(s, x) := -\phi(s, x)|x - y(s)|/(2\pi)^3$. Substituting the expression for $\hat{f}$ into equation (8), using equation (9) produces $$g(x) - \int_{R^2} \phi_1(s, x) \int_\Omega A(\xi)[w(t|x - y(s)|)(t\xi \cdot \dot{y}(s))^2 + O(\xi)] \times e^{i(H(\xi) - \xi \cdot z(s,t))} d\xi dt ds \in C_0^\infty(V),$$
(13)
$$z(s, t) := y(s) + t(x - y(s)),$$

where the integral with respect to $\xi$ is understood as an oscillatory one. For simplicity of notation, the dependence of $z(s, t)$ on x is omitted. Let I denote the integral with respect to $\xi$ in equation (13). Changing variables $\xi \to (\hat{\xi}, \lambda)$, where $\xi = \lambda(\hat{\xi}, 1)$, $$\hat{\xi} = (\hat{\xi}_1, \hat{\xi}_2), \hat{\xi}_j = \xi_j/\lambda, j = 1, 2 \text{ produces}$$
(14)
$$I = \int_0^\infty \lambda^4 \int_{\hat{\Omega}} A(\lambda(\hat{\xi}, 1))[w(t|x - y(s)|)\{t(\hat{\xi}, 1) \cdot \dot{y}(s)\}^2 + O(\lambda^{-1})] \times$$
$$e^{i\lambda(H(\hat{\xi}, 1) - (\hat{\xi}, 1) \cdot z(s, t))} d\hat{\xi} d\lambda,$$

where $\hat{\Omega}$ is a small neighborhood of the origin in $R^2$. The asymptotics of the integral with respect to $\hat{\xi}$ in equation (14) is obtained by the stationary phase method:

$$\frac{\kappa}{\lambda} A(\lambda(\hat{\xi}(s, t), 1))[w(t|x - y(s)|)\{t(\hat{\xi}(s, t), 1) \cdot \dot{y}(s)\}^2 + O(\lambda^{-1})] \times$$
(15)
$$e^{i\lambda(x_3^{(0)}(s,t) - z_3(s,t))}, \lambda \to \infty,$$

where $$x_3^{(0)}(s, t) := H_3(\hat{\xi}(s, t), 1)$$
(16)

and $\hat{\xi}(s, t)$ is obtained by solving $$H_j(\hat{\xi}, 1) = z_j(s, t), j = 1, 2.$$
(17)

In equation (15) and everywhere below $\kappa$ denotes various non-zero constants. In equation (15) the critical point on $\hat{\Omega}$ determined by equation (17) is non-degenerate and the homogeneity of $H(\xi)$:

$$H = \xi \cdot H' = \hat{\xi} \cdot H_{\hat{\xi}} + H_3 = \hat{\xi} \cdot \hat{z} + H_3,$$
(18)

so $$x_3^{(0)}(s, t) = H(\hat{\xi}(s, t), 1) - \hat{\xi}(s, t) \cdot \hat{z}(s, t),$$
(19)

where $\hat{z} = (z_1, z_2)$. Substituting equations (15) and (14) into equation (13) produces:

$$g(x) - \kappa \int_0^\infty \lambda^3 \int_{R^2} \phi_1(s, x)$$
(20)
$$A(\lambda(\hat{\xi}(s, t), 1)) \times [w(t|x - y(s)|)\{t(\hat{\xi}(s, t), 1) \cdot \dot{y}(s)\}^2 + O(\lambda^{-1})] \times e^{i\lambda\alpha(s, t)} dt ds d\lambda \in C_0^\infty(V),$$
$$\alpha(s, t) := x_3^{(0)}(s, t) - (y_3(s) + t(x_3 - y_3(s))).$$

From equations (16) and (17), $$x_3^{(0)}(s, t) = h(\hat{y}(s) + t(\hat{x} - \hat{y}(s))),$$
(21)

where $z_3 = h(z_1, z_2)$ is the local equation of S in a neighborhood of $z^{(0)}$. From equation (12), $$h_1(\hat{z}^{(0)}) = h_2(\hat{z}^{(0)}) = 0.$$
(22)

Assume first $x = x^{(0)}$ in (20). From equation (20) minus equation (22), $\alpha = 0$ and $$\alpha_s = (h_1 \dot{y}_1 + h_2 \dot{y}_2 - \dot{y}_3)(1 - t) = 0,$$
$$\alpha_t = h_1(x_1^{(0)} - y_1) + h_2(x_2^{(0)} - y_2) + y_3 = 0$$
(23)

when $s = s_0, t = t_0 := -c/(b - c)$. By assumption $b \neq c$, so $t_0$ is defined. At the critical point $$(\hat{\xi}(s_0, t_0), 1) \cdot \dot{y}(s_0) = 0.$$
(24)

From equation (12), $$a_{ss}(s_0, t_0) = \left(\frac{b}{b - c}\right)^2 (h_{11}\dot{y}_1^2 + 2h_{12}\dot{y}_1\dot{y}_2 + h_{22}\dot{y}_2^2) - \dot{y}_3 \frac{b}{b - c},$$
(25)
$$a_{st}(s_0, t_0) = b(h_{11}\dot{y}_1 + h_{12}\dot{y}_2),$$
$$a_{tt}(s_0, t_0) = h_{11}(b - c)^2,$$

so $$\det(a''(s_0, t_0)) = b[b\dot{y}_2^2(h_{11}h_{22} - 2(h_{12})^2) - \dot{y}_3 h_{11}(b - c)].$$
(26)

Hence, in addition to b=0 (i.e., $x^{(0)}=z^{(0)}$), there is at most one more point on the ray $L_+(s_0,z^{(0)})$, where $\det(\alpha'')$ can be zero.

Considering now $x=(b,0,\rho)$ in (20) and arguing similarly to A. Katsevich, "Cone Beam Local Tomography", SIAM Journal on Applied Mathematics (1999), pp. 2224-2246, gives:

$$s_0(\rho) = s_0 + O(\rho),\ t_0(\rho) = t_0 + O(\rho),\ a(s_0(\rho),t_0(\rho)) = \frac{c}{b-c}\rho + O(\rho), \quad (27)$$

where all $O(\rho)$ are smooth functions of b and $\rho$. Consequently, $$(\dot{\xi}(s_0(\rho),t_0(\rho)),1)\cdot\dot{y}(s_0(\rho)) = O(\rho). \quad (28)$$

Using equations (27) and (28), we get under the assumption $\det(\alpha'')\neq 0$:

$$g(b, 0, \rho) = \int_0^\infty \Phi(\lambda; b, \rho) e^{i\lambda \frac{c}{b-c}\rho(1+O(\rho))} d\lambda, \quad (29)$$

$$\Phi(\lambda; b, \rho) = O(\lambda^{m+1}),\ \lambda \to \infty,$$

where $\Phi$ admits an asymptotic expansion in decreasing powers of $\lambda$ as $\lambda\to\infty$. The coefficients of the expansion are $C^\infty$ functions of b and $\rho$ and the expansion can be differentiated with respect to b, $\rho$ and $\lambda$. Similarly, $O(\rho)$ in equation (29) is a smooth function of b and $\rho$.

The result analogous to equation (29) for the LT function proposed in A. K. Louis and P. Maass, "Contour reconstruction in 3-D X-ray CT", IEEE Transactions on Medical Imaging, vol. 12 (1993), pp. 764-769 (see A. Katsevich, "Cone beam local tomography", SIAM J. on Applied Mathematics, vol. 59 (1999) pp. 2224-2246) is $$g_\Lambda(b, 0, \rho) = \int_0^\infty \Phi(\lambda; b, \rho) e^{i\lambda \frac{c}{b-c}\rho(1+O(\rho))} d\lambda, \quad (30)$$

$$\Phi(\lambda; b, \rho) = O(\lambda^{m+2}),\ \lambda \to \infty.$$

Equation (30) follows immediately from equations (6.10), (6.11) in A. Katsevich, "Cone beam local tomography", SIAM J. on Applied Mathematics, vol. 59 (1999) pp. 2224-2246, if one recalls that the Fourier transform of a function in $R^3$, which is discontinuous across a smooth surface S with nonzero Gaussian curvature, is of order $O(|\xi|^{-2})$ as $|\xi|\to\infty$.

Comparing equations (29) and (30) it is shown that the function in equation (2) has non-local artifacts, which are an order of magnitude smaller. Because of the direction along which the derivative is computed in equation (2), the leading term in the expansion of $\Phi$ of order $O(\lambda^{m+2})$ disappears and the artifact is reduced.

Dynamic Local Tomography:

Consider now the case when $f$ changes with time. The parameter s in the definition of the curve C is regarded as time, it is assumed that $f$ is of the form $f(s,x)$, and the cone beam data are $$D_f(s, \alpha) = \int_0^\infty f(s, y(s) + \alpha t)dt,\ s \in I,\ \alpha \in S^2. \quad (31)$$

In the dynamic case the LT function will still be defined by equation (2). The only difference is that the data are now given by equation (31) instead of equation (1).

Even though in practice $f(s,z)$ does not vanish when $s\notin I$, to simplify the notation assume $f\in C_0^\infty(I\times V)$. Clearly, this does not result in any loss of generality, because an interval $I' \supset I$ sufficiently close to I is selected, C is extended appropriately, and $f$ is multiplied by a cut-off $\chi\in C_0^\infty(I')$, such that $\chi=1$ on I. Since $\phi\in C_0^\infty(I\times V)$, replacing $f$ by $\chi f$ will not affect g. The same argument applies when $f$ is a distribution.

First, the operator B defined by equations (31) and (2) extends to a map $E'(I\times V)\to E'(V)$.

For $\psi \in C^\infty(V) (Bf, \psi) =$ $\quad (32)$ $$\int_V \psi(x) \int_I \varphi(s, x) \times \frac{\partial^2}{\partial q^2}\left[|x-y(q)|\int_0^\infty w(t|x-y(q)|)\right.$$

$$\left. f(s, y(s) + t(x-y(q)))dt\right]\bigg|_{q=s} dsdx.$$

Changing variables $x\to z=y(s)+t(x-y(q))$, after simple transformations $$(Bf, \psi) = \int_I\int_V\left[|z-y(s)|w(t|z-y(s)|)\frac{\partial^2}{\partial q^2}\right. \quad (33)$$

$$\left.\left(\int_0^\infty \varphi(s, x(\cdot))\psi(s, x(\cdot))t^{-4}dt\right)\bigg|_{q=s}\right] \times f(s, z)dzds.$$

where $$x(\cdot) := x(z, s, q, t) = t^{-1}(z-y(s)) + y(q). \quad (34)$$

Since $\phi\in C_0^\infty(I\times V)$, t is bounded away from zero in equation (33), the expression in brackets is a $C^\infty(I\times V)$ function, and the desired assertion follows immediately by duality.

Next the relation between the wave fronts of $f$ and B$f$ is investigated without considering the most general situation, but concentrating on the practically relevant case when $f$ is a conormal distribution, which depends smoothly on s. An arbitrary $(s_0,z^{(0)},\eta^{(0)})\in I\times(T^*V\setminus 0)$ is selected. Because of linearity, the following assumptions are made about $f$ without loosing any generality.

1. supp $f$ belongs to a small neighborhood of $(s_0,z^{(0)})$;
2. For a sufficiently small open cone $\Omega\ni\eta^{(0)}$ the Fourier transform of $f(s,z)$ with respect to z satisfies:

$$\tilde{f}(s,\eta) = A(s,\eta)e^{iH(s,\eta)} + A_1(s,\eta). \quad (35)$$

3. Here

A$(s,\eta)$ is smooth, identically vanishes on $R^3$, $\Omega$, and $(\partial/\partial s)^k A(s,\eta)\in S^m(R^3)$ uniformly in s for all $k\geq 0$;

H$(s,\eta)$ is smooth (away from $\xi=0$), real-valued, and homogeneous of degree one in $\eta$;

$A_1(s,\eta)\in C^\infty$ and $(\partial/\partial s)^k A_1(s,\eta) = o(|\eta|^{-N}), |\eta|\to\infty$, uniformly in s for all $k\geq 0$ and $N\geq 0$.

When $f$ is as described above and WF(g) is a subset of all $(x,\xi)\in T^*V\setminus 0$ which satisfy $y(s)+t(x-y(s))=H_\eta(s,\eta)$ $\eta\cdot\dot{y}(s)(1-t)=H_s(s,\eta)$ $\eta\cdot(x-y(s))=0$ $\xi=t\eta$ $\quad (36)$ for some $(s,x)\in\text{supp }\phi$ and $\eta\in\Omega$.

Clearly the derivative $\partial^2/\partial q^2$ in equation (2) can be omitted when finding WF(g). From equation (35) the integral is studied $$\int_{R^3}\int_{\Omega}\int_{I}\int_{0}^{\infty} \varphi_1(s,t,x)A(s,\eta)e^{i[H(s,\eta)-\eta\cdot(y(s)+t(x-y(s)))+\xi\cdot x]}dt\,ds\,d\eta\,dx \quad (37)$$

for some smooth $\phi_1$ with compact support in the domain $t>0$. Differentiating the expression in brackets in equation (37) produces $[\cdot]_\eta = H_\eta(s,\eta) - (y(s) + t(x-y(s)))$ $[\cdot]_s = H_s(s,\eta) - \eta \cdot \dot{y}(s)(1-t)$ $[\cdot]_t = -\eta \cdot (x-y(s))$ $[\cdot]_x = \xi - t\eta.$ \quad (38)

In an embodiment, a shift between the location of a reconstruction point shown on the reconstructed image and the actual location of the point of the useful feature. The step of determining the error of the moving object is especially useful when reconstructing an image of a moving object to correct for the location of the useful features of the actual image. Suppose first that $\eta \cdot \dot{y}(s) \neq 0$ in equation (36). Then to $(z,\eta) \in \mathrm{WF}(f(s,\cdot))$ such that $y(s) \in \Pi(z,\eta) \cap C$ there corresponds $(x,\xi) \in \mathrm{WF}(g)$, where $$x = z + (z - y(s))(t^{-1} - 1), \quad (39)$$

$$\xi = t\eta, \ t = 1 - \frac{H_s(s,\eta)}{\eta \cdot \dot{y}(s)}.$$

If $\eta \cdot \dot{y}(s) = 0$ and $H_s(s,\eta) = 0$, then to $(z,\eta) \in \mathrm{WF}(f(s,\cdot))$ such that $y(s) \in \Pi(z,\eta) \cap C$ there corresponds $(x,\xi) \in \mathrm{WF}(g)$, where $x = y(s) + (z - y(s))/t,$ $\xi = t\eta, t > 0.$ \quad (40)

Thus, similarly to the static case, WF(g) consists of useful singularities described by equation (39), and of non-local artifacts, which are described by equation (40). However, as opposed to the static case, the useful singularities of g in general no longer coincide with WF(f). For example, the size of the shift between singsupp g and singsupp f depends on the quantity $H_s(s,\eta)/(\eta \cdot \dot{y}(s))$. Knowing this quantity can lead to the increased accuracy of locating singsupp f from singsupp g. If the motion of the object is approximately known, one can locate the singularities of g (represented as $(x,\xi) \in \mathrm{WF}(g)$), then estimate the quantity $H_s(s,\eta)/(\eta \cdot \dot{y}(s))$ based upon a priory information and equation (36), and then use equation (39) to find singsupp f (represented by z in that equation).

The conditions leading to the appearance of the non-local artifact are somewhat different compared with the static case as well. The ray $L_+(s,z) \subset g$ only when the additional condition $H_s(s,\eta)=0$ holds. Note that when $H_s(s,\eta) \equiv 0$, equation (36) transforms to equation (5).

Next consider the quantitative relationship between the singularities of f and g. First, lemma 3 is needed.

Suppose $\Pi(z^{(0)},\eta^{(0)}) \cap C = y(s_0)$ and $\eta^{(0)} \cdot \dot{y}(s_0) \neq 0$, where $z^{(0)} = H_\eta(s_0,\eta^{(0)})$. Find $(x^{(0)}, \xi^{(0)})$ by solving equation (36). Let $\Omega$ be a sufficiently small open cone containing $\xi^{(0)}$. Solving the system equation (36) for s,t,x, and $\eta$ in terms of $\xi \in \Omega$ determines $C^\infty(\Omega)$ functions $s(\xi), t(\xi), x(\xi),$ and $\eta(\xi)$. s,t,x are homogeneous of order 0, and $\eta$ is homogeneous of order 1.

Choose the coordinate system in which the $x_3$-coordinate is along $\eta^{(0)}$. The homogeneity of H implies $\partial^2/(\partial\eta_j\partial\eta_3)H(s,\eta)|_{\eta=\eta^{(0)}}=0, j=1,2,3$. Using equation (38), the matrix of the second derivatives evaluated at $(s_0, x^{(0)}, \eta^{(0)}, \xi^{(0)}, t)$, where t is determined from the second equation in equation (36), becomes $$D := \begin{vmatrix} H''_{11} & H''_{12} & 0 & H''_{s1} - \dot{y}_1(1-t) & -\Delta_1 & -t & 0 & 0 \\ H''_{21} & H''_{22} & 0 & H''_{s2} - \dot{y}_2(1-t) & -\Delta_2 & 0 & -t & 0 \\ 0 & 0 & 0 & H''_{s3} - \dot{y}_3(1-t) & 0 & 0 & 0 & -t \\ \dot{y}_2(1-t)] & \dot{y}_3(1-t)] & \eta_3\ddot{y}_3(1-t)] & \eta_3\dot{y}_3 & 0 & 0 & 0 \\ -\Delta_1 & -\Delta_2 & 0 & \eta_3\dot{y}_3 & 0 & 0 & 0 & -\eta_3 \\ -t & 0 & 0 & 0 & 0 & 0 & 0 \\ 0 & -t & 0 & 0 & 0 & 0 & 0 \\ 0 & 0 & -t & 0 & -\eta_3 & 0 & 0 & 0 \end{vmatrix}. \quad (41)$$

Here $\Delta_j = x_j - y_j(s)$, $H''_{jk} = \partial^2/(\partial\eta_j\partial\eta_k)H(s,\eta)$, $H''_{sj} = \partial^2/(\partial s \partial\eta_j)H(s,\eta)$, $j,k=1,2,3$. In equation (41), $\Delta_3 = 0$. After simple transformations, $$D = t^4\eta_3^2(\dot{y}_3 - H_{s3})^2. \quad (42)$$

Because of the homogeneity of H, $H_s = \xi \cdot H_{s\xi}$. Using equations (36) and (42) produces $$D = t^4(\eta \cdot \dot{y} - \eta \cdot H_{s\eta})^2 = t^4(\eta \cdot \dot{y} - H_s)^2 = t^6(\eta \cdot \dot{y})^2 > 0. \quad (43)$$

This proves that the functions $s(\xi), t(\xi), x(\xi),$ and $\eta(\xi)$ are $C^\infty$ near $\xi^{(0)}$. The statement about homogeneity follows from equation (36) and the homogeneity of H. Therefore, the functions are $C^\infty$ inside the cone $\Omega$.

Using $G(\xi) := \xi \cdot x(\xi)$, the Lagrangian submanifold $\Lambda$ of a conic neighborhood of $(x^{(0)}, \xi^{(0)})$ is defined as: $\Lambda = \{(G'(\xi), \xi): \xi \in \Omega\}$.

Again using f as previously described, suppose $\Pi(z^{(0)}, \eta^{(0)}) \cap C = y(s_0)$ and $\eta^{(0)} \cdot \dot{y}(s_0) \neq 0$. $(x^{(0)}, \xi^{(0)})$ is found by solving equation (36). Then equation (2) defines a distribution $g \in I^{m+7/4}(V, \Lambda)$, and for $|\xi| > 1$:

$$e^{iG(\xi)}\tilde{g}(\xi) + 2\pi \frac{\varphi(s,x)|x-y(s)|}{t}|\eta \cdot \dot{y}(s)|A(s,\eta) \in S^m(R^3), \quad (44)$$

where s,t,x, and $\eta$ are the functions of $\xi$ obtained by solving the system equation (36), and $A(s,\eta)$ is interpreted as 0 if no solution exists. $e^{-iG(\xi)}\tilde{g}(\xi)$ is polyhomogeneous if A is.

Similarly to equations (8) and (9), it is found that $$\tilde{g}(\sigma\xi) = -\frac{1}{(2\pi)^3} \quad (45)$$

$$\int_V \int_{R^3} \int_I \int_0^\infty \varphi(s,x)[w(t|x-y(s)|)|x-y(s)|(t\eta \cdot \dot{y}(s))^2 + O(|\eta|)] \times$$

$$A(s,\eta)e^{i[H(s,\eta)-\eta\cdot(y(s)+t(x-y(q)))+\sigma\xi\cdot x]}dt ds d\eta dx.$$

Changing variables $\eta \to \sigma\eta$ and factoring out $\sigma$, the same expression as the one in brackets in equation (37). Equation (43) implies that the signature of the matrix in equation (41) is a multiple of 4. Applying the same technique as in described in "The analysis of linear partial differential operators", to the integral with respect to $\eta$ in equation (45) and then using the stationary phase method.

This method allows us to generalize the notion of visible singularities to the dynamic case. The singularity $(z,\eta) \in WF(f(s,\cdot))$ is visible, i.e. can be stably detected from the data, if $(z-y(s))\cdot\eta=0$ and $\eta\cdot\dot{y}(s)\neq 0$. Comparing the results with equations (8) and (11), it is concluded that in both the static and dynamic cases the visible singularities of $f$ are reconstructed with the same resolution. In particular, there is no smearing due to motion in the dynamic case.

As previously described, non-local artifacts arise in the dynamic case and the strength of these artifacts is the same as in the static case.

$(z^{(0)}=H_\eta(s_0,\eta^{(0)}),\eta^{(0)}) \in WF(f)$ is selected such that the plane $\Pi(z^{(0)},\eta^{(0)})$ is tangent to $C$ at $y(s_0)$ and $H_s(s_0,\eta^{(0)})=0$. Fix $x^{(0)} \in L_+(s_0,z^{(0)})$, $x^{(0)} \notin \{z^{(0)},y(s_0)\}$ and $(s_0,x^{(0)}) \in \text{supp}\phi$. It is again assumed that $f$ is of the form previously described and the Gaussian curvature of the surface $z(\eta)=H'_\eta(s_0,\eta),\eta\in\Omega$, is nonzero near $z^{(0)}$. Subtracting equation (21) from equation (12) produces the same expression as in equation (20), but the function $x_3^{(0)}$ is now given by $$x_3^{(0)}(s,t) = h(s,\hat{y}(s)+t(\hat{x}-\hat{y}(s))). \quad (46)$$

Here $z_3 = h(s,z_1,z_2)$ is determined by solving $$H_j(s,(\hat{\xi},1)) = z_j(s,t), j=1,2, \quad (47)$$

for $\hat{\xi}=\hat{\xi}(s,t)$ (cf. (17)), and then substituting $\hat{\xi}(s,t)$ into $H'_3$ (cf. (16) and (21)):

$$h(s,z_1,z_2) := H_3(s,(\hat{\xi}(s,t),1)). \quad (48)$$

By assumption, $$h_1(s_0,\hat{z}^{(0)}) = h_2(s_0,\hat{z}^{(0)}) = 0. \quad (49)$$

Again assuming $x=x^{(0)}$, we get $\alpha=0$ and $$\alpha_s = h_s + (h_1\dot{y}_1 + h_2\dot{y}_2 - \dot{y}_3)(1-t) = 0,$$

$$\alpha_t = h_1(x_1^{(0)}-y_1) + h_2(x_2^{(0)}-y_2) + y_3 = 0 \quad (50)$$

when $s=s_0, t=t_0 := -c/(b-c)$. The additional condition $H_s(s_0,\eta^{(0)})=0$ is used which implies $h_s(s_0,\hat{z}^{(0)})=0$. The analogue of equation (25) becomes $$a_{ss}(s_0,t_0) = h_{ss} + 2(h_{s1}\dot{y}_1 + h_{s2}\dot{y}_2)\frac{b}{b-c} + \quad (51)$$

$$\left(\frac{b}{b-c}\right)^2(h_{11}\dot{y}_1^2 + 2h_{12}\dot{y}_1\dot{y}_2 + h_{22}\dot{y}_2^2) - \ddot{y}_3\frac{b}{b-c},$$

$$a_{st}(s_0,t_0) = h_{s1}(b-c) + b(h_{11}\dot{y}_1 + h_{12}\dot{y}_2),$$

$$a_{tt}(s_0,t_0) = h_{11}(b-c)^2,$$

so, $$\det(a''(s_0,t_0)) = \quad (52)$$
$$(b-c)^2(h_{ss}h_{11}-(h_{s1})^2) + 2b(b-c)\dot{y}_2(h_{11}h_{s2}-h_{s1}h_{12}) +$$
$$b[b\dot{y}_2^2(h_{11}h_{22}-2(h_{12})^2) - \ddot{y}_3 h_{11}(b-c)].$$

There are at most two more points on the ray $L_+(s_0,z^{(0)})$ (i.e., two values of b) where $\det(\alpha'')$ can be zero. Thus, under the assumption that $\det(\alpha'')\neq 0$, the same expression as in equation (29) is derived for the non-local artifact in the dynamic case.

Numerical Implementation and Experiments:

Since the LT function in equation (2) stays the same regardless of whether $f$ depends on time or not, implementation of equation (2) is identical in both the static and dynamic cases. The following description describes how equation (2) is computed when the source trajectory is a helix:

$$y_1(s) = R\cos(s-s_0), \ y_2(s) = R\sin(s-s_0), \ y_3(s) = y_3^{(0)} + \frac{h}{2\pi}s. \quad (53)$$

Here

R is the radius of the helix;

h is the pitch of the helix;

$s_0$ and $y_3^{(0)}$ are the parameters that determine the initial point on the helix; and $(y_1(s), y_2(s), y_3(s))$ are the coordinates of a point on the helix.

Following the curved detector geometry described in F. Noo, J. Pack and D. Heuscher, "Exact helical reconstruction using native cone-beam Geometries", Physics in Medicine and Biology, vol. 48, (2003), pp. 3787-3818, let $\alpha$ and w be the conventional detector coordinates: $\alpha$ is the polar angle (with the origin at the source), and w is the vertical coordinate. Hence the cone beam data are given by $D_f(s,(\alpha,w))$. Assuming that the detector contains the axis of rotation, let DP(s) denote the surface of the detector, which corresponds to the source located at y(s). In the numerical experiments it is tacitly assumed that the detector is large enough, e.g. that it contains at least the Tam window. In general, however, this is not required for LT. Let $(\alpha(q,s,x), w(q,s,x))$ be the coordinates of the point where the ray $z=y(s)+t\beta(q,x), t>0$, intersects DP(s). Similarly, let $(\alpha(s,x), w(s,x))$ be the coordinates of the projection of x onto DP(s). Clearly, $$\alpha(q,s,x)|_{q=s} = \alpha(s,x), w(q,s,x)|_{q=s} = w(s,x). \quad (54)$$

Using the chain rule:

$$g(x) = \int_I \varphi(s, x) \frac{\partial^2}{\partial q^2} D_f(s, (\alpha(q, s, x), w(q, s, x))) \Big|_{q=s} ds \qquad (55)$$

$$\cong \int_I \varphi(s, x) \left( c_\alpha^2 \frac{\partial^2}{\partial \alpha^2} + 2 c_\alpha c_w \frac{\partial^2}{\partial \alpha \partial w} + c_w^2 \frac{\partial^2}{\partial w^2} \right) D_f(s, (\alpha, w)) \Big|_{\substack{a=\alpha(s,x)\\w=w(s,x)}} ds,$$

is obtained from equation (2) where $$c_\alpha = \frac{\partial \alpha(q, s, x)}{\partial q} \Big|_{q=s}, \qquad c_w = \frac{\partial w(q, s, x)}{\partial q} \Big|_{q=s}, \qquad (56)$$

and $\cong$ denotes equality up to the leading singular term. The terms omitted on the right in equation (55) contain, at most, the first order derivatives of $D_f$, so that the results previously obtained apply to the new function.

Using the approach described in id., for $\alpha(q,s,x)$ and $w(q,s,x)$:

$$\tan \alpha(q, s, x) = \frac{y_1(s)(x_2 - y_2(q)) - y_2(s)(x_1 - y_1(q))}{y_1(s)(x_1 - y_1(q)) - y_2(s)(x_2 - y_2(q))}, \qquad (57)$$

$$w(q, s, x) = R \frac{x_3 - y_3(q)}{\sqrt{(x_1 - y_1(q))^2 + (x_2 - y_2(q))^2}}.$$

Recall that:

$$V(s, x) := R - \frac{x_1 y_1(s) + x_2 y_2(s)}{R}, \qquad (58)$$

$$\tan \alpha(s, x) = \frac{x_2 y_1(s) + x_1 y_2(s)}{RV(s, x)},$$

$$w(s, x) = R \cos \alpha(s, x) \frac{x_3 - y_3(s)}{V(s, x)}.$$

Differentiating equation (57) with respect to q and using equations (58) and (54), after some transformations, it is found that $$c_\alpha = -\frac{R \cos^2 \alpha(s, x)}{V(s, x)}, \quad c_w = \frac{R \cos \alpha(s, x)}{V(s, x)} \left( w(s, x) \sin \alpha(s, x) - \frac{h}{2\pi} \right). \Box^* \qquad (59)$$

In general, there is a significant flexibility in selecting the function $\varphi(s,x)$. By choosing the appropriate $\varphi(s,x)$, a LT can be adopted for practically any scan geometry, including truncated projections, incomplete or segmented source trajectory, etc. A possible candidate, which guarantees the reconstruction of all visible singularities and is efficient from the computational point of view is determined. Let $w=w_{bot}(\alpha)$ and $w=w_{top}(\alpha)$ be the equations of the top and bottom boundaries of the Tam window on the detector. Choose any $\chi \in C_0^\infty(R)$ such that $\chi \equiv 1$ on $[0,1]$, and define $$\varphi(s, x) = \chi \left( \frac{w_{top}(\alpha) - w}{w_{top}(\alpha) - w_{bot}(\alpha)} \right) \Big|_{\substack{a=\alpha(s,x)\\w=w(s,x)}}. \qquad (60)$$

By construction, $\varphi(s,x)>0$ whenever $s \in I_\pi(x)$ (the $\pi$-interval of x). This property guarantees that the visible singularities of $f$ are detected (see equations (11) and (44)). The advantage of equation (60) is that $\varphi(s,x)$ only depends on the projection of x onto DP(s), so the function is written in the form $\varphi(\alpha(s,x), w(s,x))$. Equation (59) is used to rewrite equation (55) in the form $$g(x) = \int_I \frac{R^2}{V^2(s, x)} \Phi(s; \alpha(s, x), w(s, x)) ds, \qquad (61)$$

$$\Phi(s; \alpha, w) =$$

$$\varphi(\alpha, w) \cos^2 \alpha \left[ \cos^2 \alpha \frac{\partial^2}{\partial \alpha^2} - 2 \cos \alpha (w \sin \alpha - h/(2\pi)) \frac{\partial^2}{\partial \alpha \partial w} + (w \sin \alpha - h/(2\pi))^2 \frac{\partial^2}{\partial w^2} \right] D_f(s, (\alpha, w)).$$

As is seen, equation (61) admits a very efficient filtered-backprojection implementation. Moreover, the filtering step consists only of computing derivatives, i.e. is local.

For comparison purposes the LT function is computed which is analogous to the one described in A. K. Louis and P. Maass, "Contour reconstruction in 3-D X-ray CT", IEEE Transaction on Medical Imaging, vol. 12 (1993) pp. 764-769 as:

$$g_\Lambda(x) = \int_I \varphi(s, x) \Delta_x D_f(s, (\alpha(s, x), w(s, x))) ds \qquad (62)$$

$$\cong \int_I \varphi(s, x) \left( |\nabla_x \alpha(s, x)|^2 \frac{\partial^2}{\partial \alpha^2} + 2(\nabla_x \alpha(s, x) \cdot \nabla_x w(s, x)) \frac{\partial^2}{\partial \alpha \partial w} + |\nabla_x w(s, x)|^2 \frac{\partial^2}{\partial w^2} \right) D_f(s, (\alpha, w)) \Big|_{\substack{a=\alpha(s,x)\\w=w(s,x)}} ds,$$

Using equation (58) produces $$\nabla_x \alpha(s, x) = \frac{\cos \alpha}{RV} (y_1 \sin \alpha - y_2 \cos \alpha, y_1 \cos \alpha + y_2 \sin \alpha, 0) \Big|_{\substack{a=\alpha(s,x)\\V=V(s,x)}}, \qquad (63)$$

$$\nabla_x w(s, x) = \frac{\cos \alpha}{RV} (w(y_1 \cos \alpha + y_2 \sin \alpha), w(-y_1 \sin \alpha + y_2 \cos \alpha), R^2) \Big|_{\substack{a=\alpha(s,x)\\V=V(s,x)\\w=w(s,x)}}.$$

After simple calculations, equation (63) implies $$|\nabla_x \alpha|^2 = \left(\frac{\cos\alpha}{V}\right)^2, \nabla_x \alpha \cdot \nabla_x w = 0, |\nabla_x w|^2 = \left(\frac{\cos\alpha}{V}\right)^2 (R^2 + w^2). \quad (64)$$

Finally, substitution of equation (64) into equation (62) yields $$g_\Lambda(x) = \int_I \frac{1}{V^2(s,x)} \Phi_\Lambda(s; \alpha(s,x), w(s,x)) ds, \quad (65)$$

$$\Phi_\Lambda(s; \alpha, w) = \varphi(\alpha, w)\cos^2\alpha \left[\frac{\partial^2}{\partial \alpha^2} + (R^2 + w^2)\frac{\partial^2}{\partial w^2}\right] D_f(s, (\alpha, w)).$$

FIG. 1 is a flow diagram of the steps for the cone beam local tomography according to the present invention. In step 10 the current cone beam projection is loaded into computer memory with the assumption that the CB projection loaded into computer memory corresponds to the x-ray source located at y(s). Using the CB projection data $D_f(y(s),(\alpha,w))$ in step 20, the combination of derivatives that will result in suppression of the artifacts of the image is determined, wherein the combination of derivatives corresponds to the differentiation of the data along the direction tangent to the curve. Based on the determined combination direction, the cone beam projection data is differentiated. In this example, the derivatives $$\frac{\partial^2}{\partial \alpha^2} D_f(s, (\alpha_i, w_j)), \frac{\partial^2}{\partial \alpha \partial w} D_f(s, (\alpha_i, w_j)), \frac{\partial^2}{\partial w^2} D_f(s, (\alpha_i, w_j))$$

are found for all $(\alpha_i, w_j)$ on the detector. The computation can be accomplished using interpolation and finite differences. Thus, step 20 includes finding the combination of derivatives that will result in reduced artifacts and then computing the derivatives, in other words, it is local.

In step 30, the derivative results are processed to compute the determined combination of the derivatives. In this example, the derivatives are multiplied by the quantities $\cos^2 \alpha$, $-2\cos\alpha(w\sin\alpha - h/(2\pi))$, and $(w\sin\alpha - h/(2\pi))^2$, respectively, for all $(\alpha_i, w_j)$ on the detector. Then the results are multiplied by $\phi(\alpha_i, w_j)\cos^2 \alpha_i$ to produce the function $\Phi(s; \alpha_i, w_j)$ according to equation (61), where the function $\phi(\alpha, w)$ is determined using equation (60) and the relation $\phi(\alpha(s,x), w(s,x))=\phi(s,x)$. By construction, $\phi(s,x)>0$ whenever $s \in I_\pi(x)$ (the π-interval of x). This property guarantees that the visible singularities of ƒ are detected. The advantage of equation (60) is that $\phi(s, x)$ only depends on the projection of x onto DP(s), so the function is written in the form $\phi(\alpha(s,x), w(s,x))$.

Figure 2:
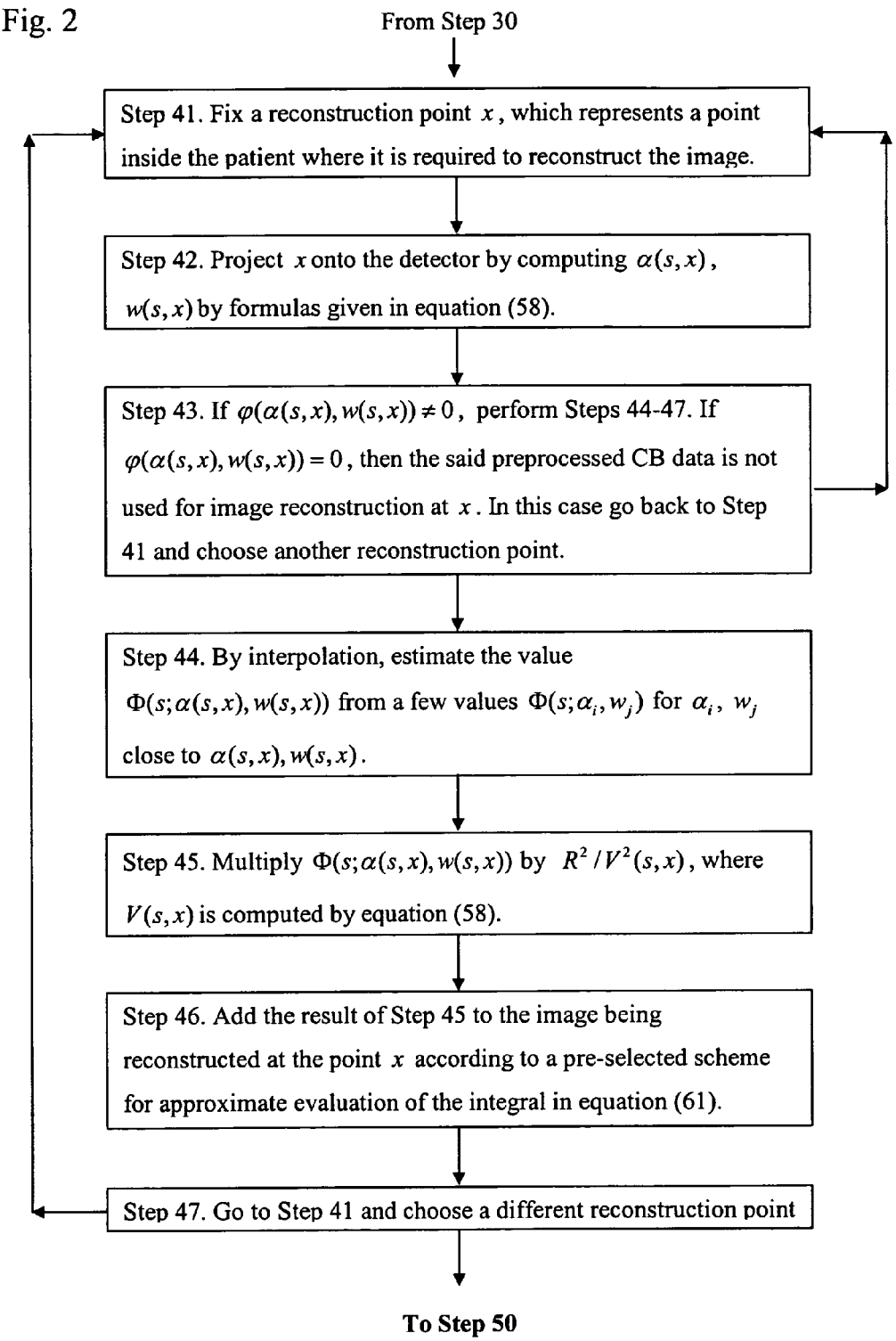
FIG. 2 is flow diagram for the back-projection substeps corresponding to step 40 of FIG. 1.

In backprojection step 40, for each reconstruction point x, the data found in step 30 is back-projected according to the first line of equation (61). FIG. 2 is a seven substep flow diagram for backprojection, which corresponds to step 40 of FIG. 1. In step 41, a reconstruction point x is fixed, which represents a point inside the patient where it is required to reconstruct the image. The reconstruction point x is projected onto the detector in step 42 by computing $\alpha(s,x)$, $w(s,x)$ by formulas given in equation (58). In step 43 it is determined if $\phi(\alpha(s,x), w(s,x))=0$. If $\phi(\alpha(s,x), w(s,x))=0$, then the preprocessed CB data is not used for image reconstruction at x and step 41 is repeated for a different reconstruction point. If $\phi(\alpha(s,x), w(s,x)) \neq 0$, then the filtered CB data affects the image at x and steps 44-47 are performed.

In step 44, the value $\Phi(s;\alpha(s,x), w(s,x))$ is estimated by interpolation from a few values $\Phi(s;\alpha_i,w_j)$ for $\alpha_i,w_j$ close to $\alpha(s,x)$, $w(s,x)$. $\Phi(s;\alpha(s,x), w(s,x))$ is multiplied by $$\frac{R^2}{V^2(s,x)}$$

in step 45, where V(s,x) is computed by equation (58). The result of step 45 is added to the image being reconstructed at the point x in step 46 according to a pre-selected scheme (for example, the Trapezoidal scheme) for approximate evaluation of the integral in equation (61). In step 47, go to step 41 and select a different reconstruction point x. After repeating steps 41-47 for each reconstruction point inside the area of interest, the process advances to step 50.

Referring back to FIG. 1, steps 10-40 are repeated until the scan is finished or when the image reconstruction process is complete for the required points of the area of interest to reconstruct the useful features. At step 50, the process returns to step 10 shown in FIG. 1 to load the next CB projection data into computer memory. The image can be displayed at all reconstruction points x for which the image reconstruction process has been completed, that is, when subsequent CB projections are not necessary for reconstructing the image at those points. The CB projection that have already been processed is no longer needed for image reconstruction and is discarded from the computer memory. The algorithm concludes when the scan is finished or the image reconstruction process has completed at all the required points.

For LT function testing, experiments were performed. Table 1 provides simulation and reconstruction parameters used for the experiments.

TABLE 1

| Simulation and reconstruction parameters | |
|---|---|
| R (radius of the spiral) | 600 mm |
| h (pitch of the spiral) | 66 mm |
| detector pixel size (as projected to isocenter) | $10^{-3}$ rad × 0.6 mm |
| number of detector rows | 128 |
| number of detectors per row | 950 |
| number of source positions per rotation | 1000 |
| voxel size in each direction | 1.0 mm |

Figure 3A:
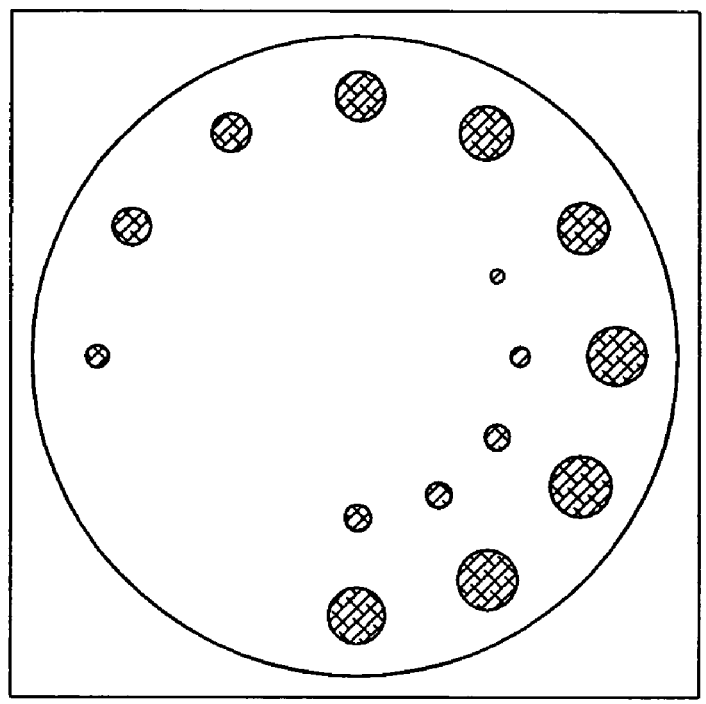
FIG. 3a shows the new LT function g in the case of the clock phantom.
Figure 3B:
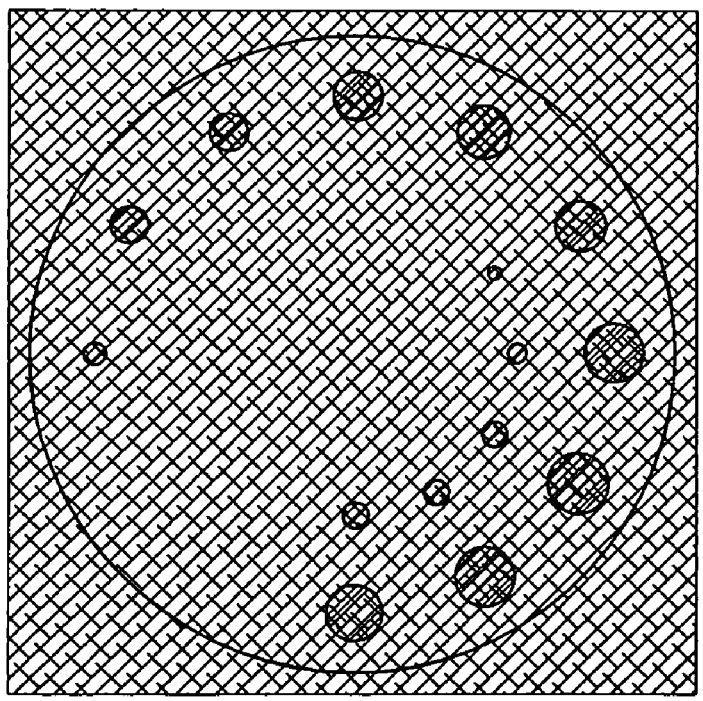
FIG. 3b shows old LT function $g_A$ in the case of the clock phantom.

FIGS. 3a and 3b show the results of reconstructing the conventional clock phantom as described in A. Katsevich, Samit Basu, and Jiang Hsieh, "Exact filtered backprojection reconstruction for dynamic pitch helical cone beam computed tomography", Physics in Medicine and Biology, vol. 49 (2004) pp. 3089-3103. The original clock phantom, which is slightly different from the one used here is described in H. Turbell and P. E. Danielsson, "Helical cone beam tomography", Int. Journal of Imaging System and Technology, vol. 11 (2000), pp. 91-100.

Figure 4A:
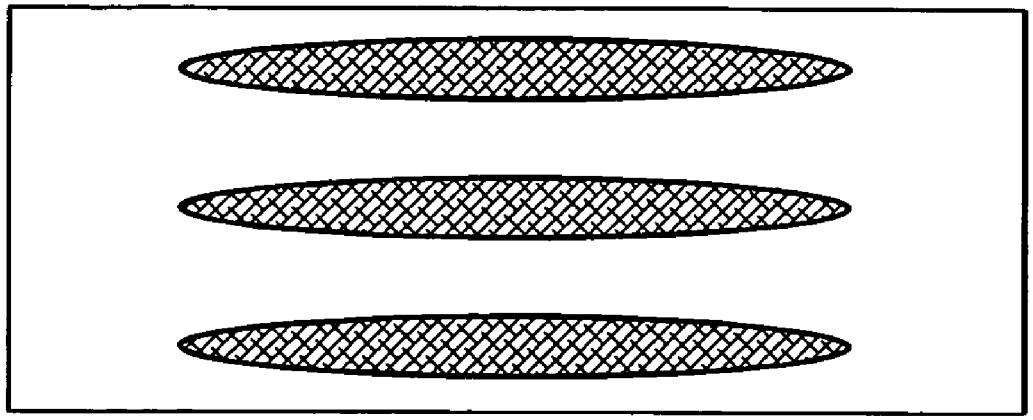
FIG. 4a shows the results of reconstructing the three-disk phantom according to the present invention.
Figure 4B:
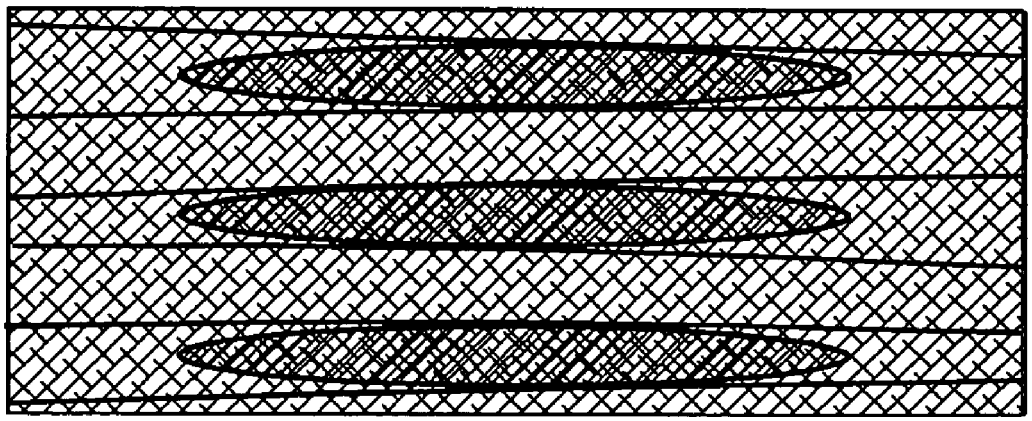
FIG. 4b shows the results of reconstructing the three-disk phantom according to the prior art.

FIG. 4a shows the LT function g according to the present invention and FIG. 4b shows the LT function $g_\Lambda$ according to the prior art. FIG. 4a shows the results of reconstructing the phantom, which consists of three elongated ellipsoids with half-axes 100×100×10 (all the sizes and coordinates are given in mm). The locations of their centers are (0,0,−40), (0,0,0), and (0,0,40), and the cross-section $|x_1| \leq 150, x_2=0, |x_3| \leq 60$ is shown.

Figure 5A:
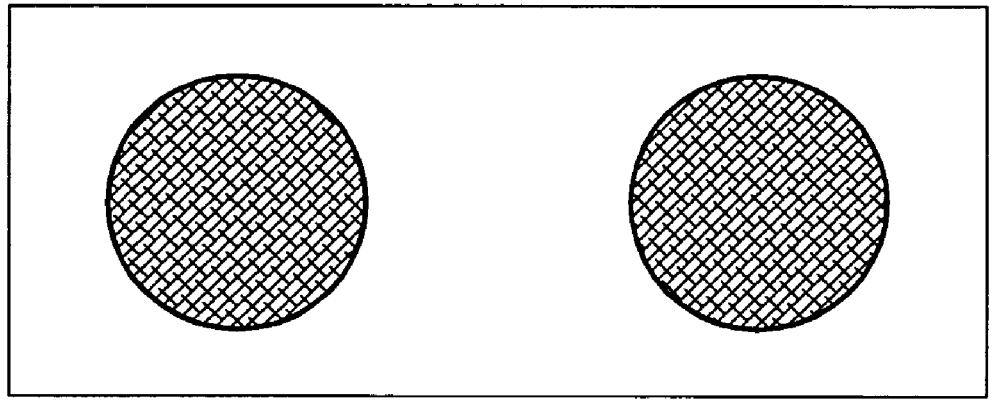
FIG. 5a shows the results for a phantom consisting of two identical balls having radius 40 centered at (−80,0,0) and (80,0,0), respectively, according to the present invention.
Figure 5B:
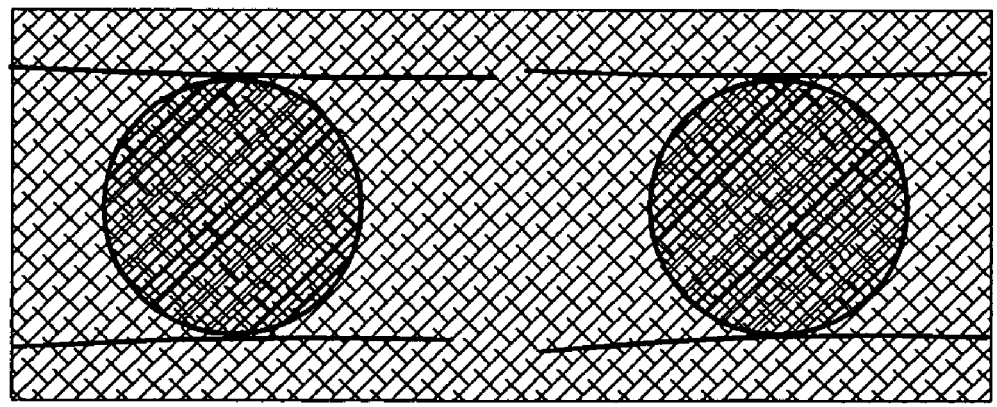
FIG. 5b shows the results for a phantom consisting of two identical balls having radius 40 centered at (−80,0,0) and (80,0,0), respectively, according to the prior art.

FIGS. 5a and 5b show the results for another phantom according to another experiment. The phantom in this embodiment consists of two identical balls having radius 40 centered at approximately (−80,0,0) and approximately (80, 0,0), respectively. As is seen from the figures, the non-local artifacts in g are weaker than those in $g_A$. Reconstruction of the clock phantom with the cross-section $|x_1|\leq 255.5$, $|x_2|\leq 255.5, x_3=0$ is shown in FIG. 3a. FIG. 3a shows the LT function g according to the present invention and FIG. 3b shows the LT function $g_A$ according to the prior art.

Figure 6A:
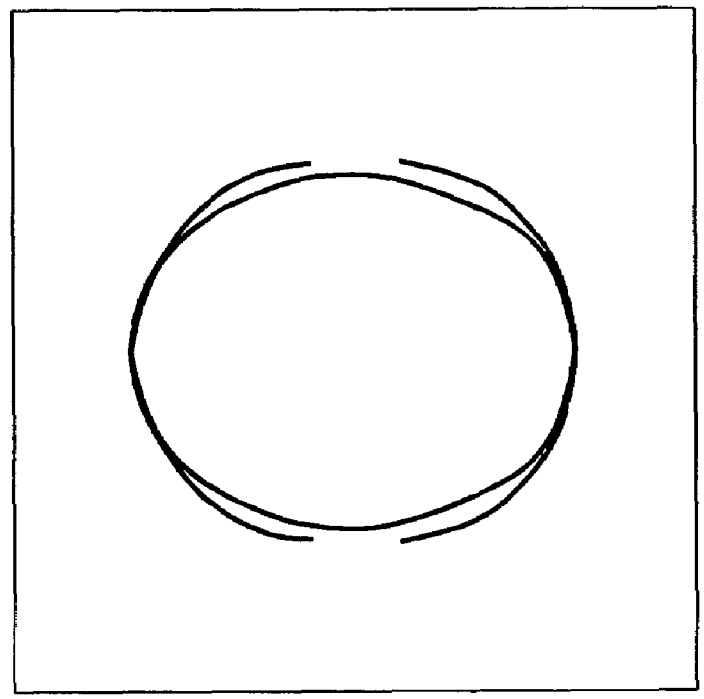
FIG. 6a shows reconstruction of an ellipsoid in the dynamic case, new LT function g according to the present invention wherein the ellipsoid moves either up or down.

Reconstructions in the dynamic case are shown in FIGS. 6 and 7 wherein the phantom is represented by a single ellipsoid $$\left(\frac{x_1 - x_1(s)}{a(s)}\right)^2 + \left(\frac{x_2 - x_2(s)}{b(s)}\right)^2 + \left(\frac{x_3 - x_3(s)}{c(s)}\right)^2 \leq 1, \quad (66)$$

wherein the half-axes (a(s), b(s), c(s)) and the center ($x_1$(s), $x_2$(s),$x_3$(s))—depend on time. For FIG. 6a:

$$a(s)=b(s)=c(s)=50, \quad (20)$$

$$x_1(s)=x_2(s)=0, x_3(s)=10\sin(s/3). \quad (67)$$

Figure 6B:
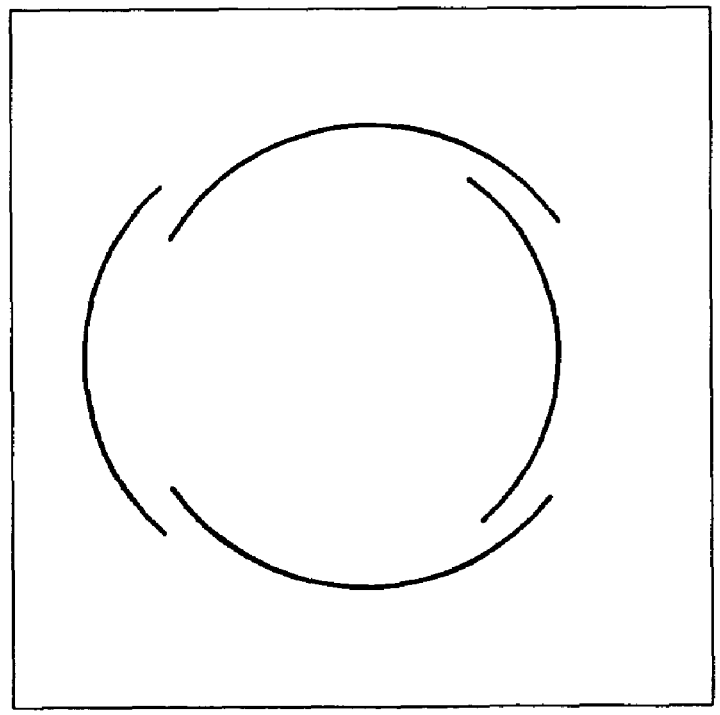
FIG. 6b shows reconstruction of an ellipsoid in the dynamic case, new LT function g according to the present invention wherein the ellipsoid moves either left or right

For FIG. 6b:

$$a(s)=b(s)=c(s)=50, \quad (25)$$

$$x_1(s)=10\cos(s/3), x_2(s)=x_3(s)=0. \quad (68)$$

Figure 7A:
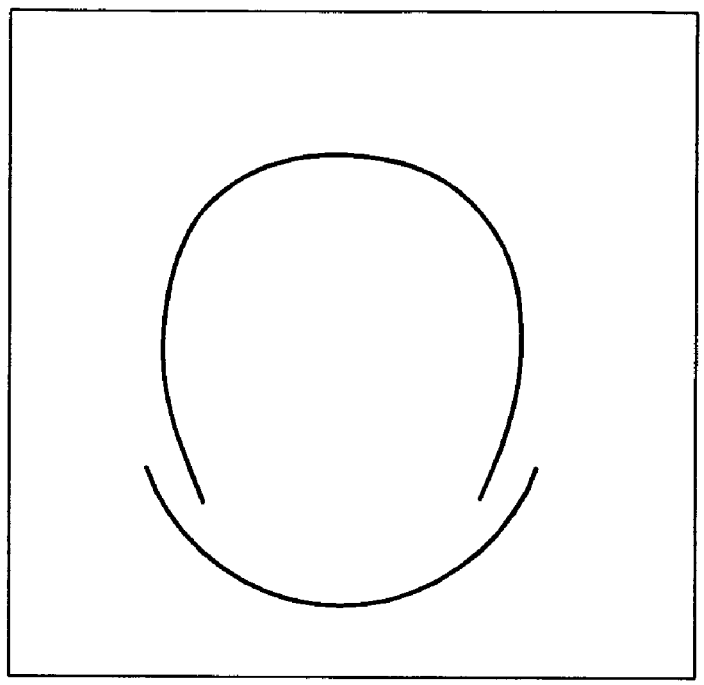
FIG. 7a shows reconstruction of an ellipsoid in the dynamic case, new LT function g according to the present invention wherein the ellipsoid expands and contracts.

For FIG. 7a:

$$a(s)=b(s)=50(1+0.2\cos(s/3)), c(s)=50(1+0.2\sin(s/3)),$$
$$x_1(s)=x_2(s)=x_3(s)=0. \quad (69)$$

Figure 7B:
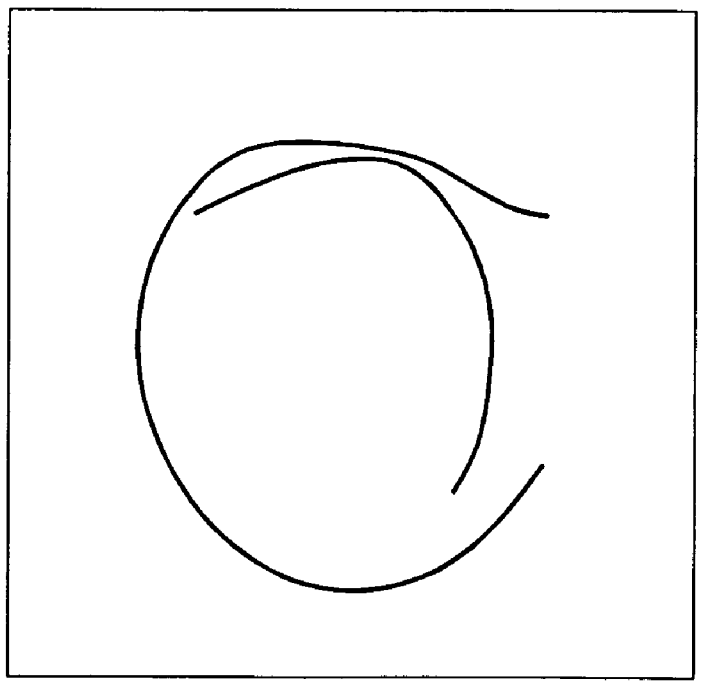
FIG. 7b shows reconstruction of an ellipsoid in the dynamic case, the prior art LT function g wherein the ellipsoid expands and contracts as well as moves left-right.

For FIG. 7b:

$$a(s)=b(s)=50(1+0.2\cos(s/3)), c(s)=50(1+0.2\sin(s/3)),$$
$$x_1(s)=10\cos(s/3), x_2(s)=x_3(s)=0. \quad (70)$$

The results of dynamic reconstructions confirm that the visible singularities are reconstructed with about the same resolution as in the static case, and that no additional artifacts arise because of the changes in the phantom. As soon as some singularity of $f$ becomes "invisible" due to motion, the corresponding singularity in g ends at that point, but this does not cause any streaks across the image. Equivalently we can say that LT is quite stable with respect to inconsistencies in the data caused by motion.

The images shown in FIGS. 6 and 7 were obtained by ignoring the dynamic nature of the phantom during reconstruction. Clearly, it is theoretically impossible to stably reconstruct an accurate 4D image of $f$ (3D+time) from the cone beam data with only three degrees of freedom. On the other hand, in many cases one can use additional information for improving image quality. Consider, for example, cardiac imaging based on a circular source trajectory, which is of significant importance in medical CT.

Using the electro cardiogram (ECG) of the patient, which is measured concurrently with cone beam projections, the data corresponding to a fixed cardiac phase (e.g., when the heart is at rest) is accumulated from multiple source rotations and then LT reconstruction is performed from that data. Moreover, the problem of 4D CT imaging can be approximately solved. Using again the ECG data, the complete cardiac cycle is split into several segments, accumulates the cone beam data for each segment from multiple source rotations, and then applies LT separately for each segment. See F. Koo, H. Kudo and L. Zeng, Proceedings of the VIIIth International Conference on Fully Three-Dimensional Reconstruction in Radiology and Nuclear Medicine, Salt Lake City, Utah, University of Utah, (2005), where similar techniques are used together with more conventional inversion algorithms.

Because of the flexibility of LT, its relative stability with respect to inconsistencies in the data (compared with "global" algorithms) and the ability to accurately reconstruct edges inside objects, it is expected that LT can become a valuable tool, which provides important information complementing well-established inversion techniques.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of reconstructing an image from cone beam (CB) projection data provided by at least one detector, comprising the steps of:
   collecting CB projection data of an object;
   storing the collected CB projection data in a memory; and
   reconstructing the image of the object from a local CB projection data including the steps of:
   filtering the local cone beam projection data using only derivative operations; and
   backprojection updating of the image to reconstruct the image with artifacts having a strength that is weaker than the strength of the useful features, the useful features being high spatial contrast features in the image which reflect the corresponding high spatial contrast features in the object.

2. The method of claim 1, wherein the reconstructing step comprises the step of:
   finding a combination of only derivatives of the CB projection data that weaken the artifacts.

3. The method of claim 2, wherein the finding a combination of derivatives of the CB projection data step comprises the steps of:
   collecting cone beam data that represents a collection of integrals with or without weight of an unknown function that represents the object being scanned, wherein said integrals are over lines and said lines intersect a curve; and
   finding the combination of derivatives of the CB projection data that is equivalent to differentiating the data along a direction which is tangent to a source trajectory.

4. The method of claim 3, further comprising the step of:
   computing the combination of derivatives of the CB projection data, which is equivalent to differentiating the data along the direction of the tangent of the source trajectory.

5. The method of claim 4, wherein the differentiation step comprises the step of:
   computing derivatives $$\frac{\partial^2}{\partial \alpha^2} D_f(s, (\alpha, w)), \frac{\partial^2}{\partial \alpha \partial w} D_f(s, (\alpha, w)), \frac{\partial^2}{\partial w^2} D_f(s, (\alpha, w))$$

each CB projection data, wherein
   $\alpha$ is the angular parameter on the detector,
   w is the vertical parameter on the detector,
   s is the parameter along the source trajectory,
   x is the point where image reconstruction is performed, $D_f(s,(\alpha, w))$ is the CB projection data, and
$f$ is the function representing the object being scanned.

6. The method of claim 5, wherein the reconstruction step further comprises the steps of:
   multiplying the derivatives by the quantities $\cos^2 \alpha$, $-2\cos\alpha(w\sin\alpha - h/(2\pi))$, and $(w\sin\alpha - h/(2\pi))^2$, respectively;
   adding the multiplied derivatives to produce a combination of derivatives;
   multiplying the combination of derivatives by $\phi(\alpha,w)\cos^2\alpha$ to produce the function $\Phi(s; \alpha, w)$ according to $$\Phi(s; \alpha, w) = \varphi(\alpha, w)\cos^2\alpha \left[\cos^2\alpha \frac{\partial^2}{\partial \alpha^2} - 2\cos\alpha(w\sin\alpha - h/(2\pi))\frac{\partial^2}{\partial \alpha \partial w} + (w\sin\alpha - h/(2\pi))^2 \frac{\partial^2}{\partial w^2}\right] D_f(s, (\alpha, w)),$$

computing the CB local tomography function $$g(x) = \int_I \frac{R^2}{V^2(s, x)} \Phi(s; \alpha(s, x), w(s, x))ds,$$

wherein the source trajectory is a helix, and
   R is the radius of the helix,
   h is the pitch of the helix,
   $\alpha(s, x), w(s, x)$ are, respectively, the $\alpha$ and w coordinates of the point x projected onto detector, which corresponds to the point s of the source trajectory,
   $\phi(s, x)$ is a cut-off function which determines the portion of the source trajectory that is used for image reconstruction at x,
   $\phi(\alpha, w)$ is the function determined by the relation $\phi(\alpha(s, x), w(s, x)) = \phi(s, x)$, $$V(s, x) = R - \frac{x_1 y_1(s) + x_2 y_2(s)}{R},$$

$x_1, x_2$ are two coordinates of the point x, and
$y_1(s), y_2(s)$ are two coordinates of the point s of the source trajectory.

7. The method of claim 4, further comprising the step of:
   processing the derivative result by multiplying it by a weight to produce a processed data.

8. The method of claim 1, further comprising the step of:
   determining a shift between a location of the reconstruction point shown on the reconstructed image and an actual location of a corresponding useful feature of the object to determine a location error of a moving object to correct for the location of the useful features of the object.

9. A system for reconstructing an image of an object comprising:
   a scanner for scanning the object in three-dimensions to produce a cone beam projection data;
   a processing unit having a memory for storing the cone beam projection data and executing instructions;
   a first set of instructions for calculating derivatives of the cone beam projection data;
   a second set of instruction for reconstructing useful features of the image from a local cone beam projection data including:
      a first subset of instructions to filter the local cone beam projection data consisting only of derivative operations; and
      a second subset of instructions to backprojection update the filtered local cone beam projection data to reconstruct the image with suppressed artifacts that are weaker than the strength of the useful features, the useful features being high spatial contrast features in the reconstructed image corresponding to the high spatial contrast features in the object; and
   a display connected with said processing unit for displaying the reconstructed image.

10. The system of claim 9, wherein the first subset of instructions includes instructions for differentiating the cone beam projection data along a direction tangent to the curve that represents the scanner trajectory.

11. The system of claim 9, wherein the first set of instructions comprises:
   a third subset of instructions for finding a direction of the derivative of the cone beam projection data that will result in suppressed artifacts; and
   a fourth subset of instructions for differentiating the cone beam projection data according to the direction.

12. The system of claim 9, further comprising:
   a third set of instructions for determining a shift between a location of the reconstruction point shown on the reconstructed image and an actual location of the point on the object to correct for the location of the useful features of the actual image.

13. A method for cone beam local tomography comprising the steps of:
   loading current cone beam projection data of an object into a computer memory, wherein the cone beam projection data corresponds to a focus of beams of radiation located at y(s), wherein y(s) is a curve along which a source of radiation moves relative to an object being scanned;
   calculating derivatives of the cone beam projection data in a direction that results in suppression of the artifacts;
   processing the derivative results of a local cone beam projection data to reconstruct the image with suppressed artifacts that have a strength weaker than the strength of the useful features that are high spatial contrast features corresponding to the high spatial contrast features of the object;
   applying back projection to the processed data; and
   displaying the reconstructed image with suppressed artifacts without suppressing the strength of useful features.

14. The method of claim 13, wherein the differentiation step comprises the steps of:
   determining a direction of the derivative that results in suppression of the artifacts, wherein the direction is tangent to the curve y(s); and
   calculating derivatives of the cone beam projection data along the direction tangent to the curve y(s) to suppress artifacts.

15. A method of reconstructing an image from local cone beam (CB) data provided by at least one detector, comprising the steps of:
   collecting CB projection data of an object;
   storing the collected CB projection data in a memory;
   reconstructing the image from the local CB projection data, wherein for each reconstruction point x the local cone beam is defined as data corresponding to rays of radiation passing through a small neighborhood of the point x, the size of the small neighborhood not exceeding that which is required to numerically compute a derivative at each reconstruction point; and wherein artifacts of the reconstructed image have a weaker strength than the strength of the useful features, the useful features being high spatial contrast features in the reconstructed image that correspond to the high spatial contrast features in the object.

* * * * *